United States Patent [19]

Barnes et al.

[11] Patent Number: 4,689,235

[45] Date of Patent: Aug. 25, 1987

[54] ENCAPSULATION MATRIX COMPOSITION AND ENCAPSULATE CONTAINING SAME

[75] Inventors: Janette M. Barnes; James A. Steinke, both of Jacksonville, Fla.

[73] Assignee: SCM Corporation, Iselin, N.J.

[21] Appl. No.: 692,486

[22] Filed: Jan. 18, 1985

Related U.S. Application Data

[63] Continuation-in-part of Ser. No. 575,654, Jan. 31, 1984, abandoned.

[51] Int. Cl.$^4$ ...................... A23L 1/221; A23L 1/222; A23P 1/04; A23P 1/12
[52] U.S. Cl. ...................................... 426/89; 426/103; 426/650; 426/651; 426/661; 426/516
[58] Field of Search ................. 426/89, 103, 650, 651, 426/661, 516

[56] References Cited

U.S. PATENT DOCUMENTS 3,041,180  6/1962  Swisher ............................... 426/651
3,704,137  11/1972  Beck .................................... 426/651
3,974,033  8/1976  Harjes et al. ........................ 426/661
3,989,852  11/1976  Palmer ................................ 426/289
4,232,047  11/1980  Sair et al. ............................ 426/96

FOREIGN PATENT DOCUMENTS 0070719  1/1983  European Pat. Off. ............ 426/103

OTHER PUBLICATIONS

Windholz et al., *The Merck Index*, 10th ed., Merck & Co. Inc., Rahway N.J., pp. 1130 and 1131, ©1983.

*Primary Examiner*—Thomas G. Wiseman
*Assistant Examiner*—Elizabeth C. Weimar
*Attorney, Agent, or Firm*—Richard H. Thomas

[57] ABSTRACT

There is provided an extrudable encapsulation matrix composition having improved loading capacity for oils, flavors, fragrances, agricultural chemicals, insecticides, drugs, etc. The matrix comprises a maltodextrin and hydrogen octenylbutanedioate amylodextrin or equivalent.

28 Claims, No Drawings

ENCAPSULATION MATRIX COMPOSITION AND ENCAPSULATE CONTAINING SAME

This application is a continuation-in-part of prior application Ser. No. 575,654, now abandoned filed on Jan. 31, 1984, and assigned to assignee of the present application.

This invention relates to encapsulation, and more particularly a matrix composition for encapsulating an active ingredient at high loading levels. The active ingredient may be an organoleptic material, an agricultural chemical, or a physiologically active material, e.g., a drug or insect control agent.

BACKGROUND OF THE INVENTION

A particular problem with prior art encapsulation matrices has been their inability to hold more than about 10% by weight of an encapsulate or dispersed phase, such as an essential oil. Accordingly, a principal object of the present invention is to provide an improved matrix composition adapted for extrusion and further having an improved capacity to contain in a stable manner a normally liquid dispersed phase, such as an organoleptic material, e.g., lemon oil, orange oil, or the like.

This improvement arose out of work originally done by Beck as described in U.S. Pat. No. 3,704,137 dated Nov. 28, 1972. This patent describes certain relatively stable particulate essential oil-containing compositions and a process for making the solid particulate material. The procedural steps described by Beck can be used in preparing the novel encapsulates of the present invention. We have found that the load carrying capacity of the Beck material is below about 10% by weight. It has been found that increased loading capacity can be achieved by formulating a matrix composition to contain (a) maltodextrin, a starch hydrolysate, and (b) a modified starch which is a derivative of waxy maize. The composition is characterized by high load capacity for an active ingredient, and handleability according to the Beck procedure, supra, at reasonable pressures and temperatures. A similar procedure is disclosed in Swisher U.S. Pat. No. 3,041,180.

Currently, modified starches are used in the production of spray dried flavors, but they are not used commercially as an ingredient in extrusion encapsulation process formulations. These encapsulation processes are basically different. In encapsulating by spray drying, flavorant and emulsifier are added directly to the encapsulation matrix consisting of water, maltodextrin, gum arabic, etc. Water is then removed by spray drying. The product is porous and not as stable as that produced by extrusion technology. In the latter case, water is removed before flavor is added and locked in as in U.S. Pat. No. 3,704,137, supra. Extrusion products have superior shelf stability. However, until the present invention, active ingredient loadings available in extrusion were much lower (9–10%) than the 15 to 25% levels typical of spray dried products. According to the present invention, the advantages of extrusion encapsulation such as stability can be realized and loadings of up to 20–35 or 40% achieved. Still further, certain of the prior art encapsulation procedures require substantial extrusion pressures and equipment capable of handling such pressures. These pressures are commonly above 1000 psi, e.g., 3000 to 4000 psi. The present invention allows extrusion to occur at pressures below 150 psig. and generally below 100 psig.

Various methods of producing maltodextrins are known. Maltodextrins are identified by Chemical Abstracts Registry No. 9050-36-6. Reference may be had to U.S. Pat. No. 3,974,033 to Harjes et al dated Aug. 10, 1976 and to the prior art discussed therein. The maltodextrins useful herein have a low DE (dextrose equivalent), i.e., in the range of 3 to 40. Generally, they are made by first liquefying native starch with an acid or an enzyme to a DE less than about 15, followed by enzymatic conversion, e.g., with bacterial alpha-amylase (See U.S. Pat. No. 3,849,194 and Re. 30,880). As pointed out in U.S. Pat. No. 3,974,033, maltodextrins are first prepared in syrup form and then spray dried to a moisture content of 3–5% by weight. These prior art maltodextrin materials and those prepared from oxidized starch as described in U.S. Pat. No. 3,974,033 are useful herein.

The second principal ingredient of the improved matrix compositions hereof is a derivative of waxy maize identified as hydrogen octenylbutanedioate amylodextrin. It has a Chemical Abstracts Registry Number 61932-62-5. This material is commercially available from National Starch and Chemical Corp. as "Capsul". "Capsul" has been used as an encapsulating agent in spray drying techniques. (See "Modified Starch Encapsulating Agents Offer Superior Emulsification, Film Forming, and Low Surface Oil" by King et al, Food Product Development, Volume 10, No. 10, pages 54, 56, 57, December, 1976; and Sair et al U.S. Pat. No. 4,232,047, particularly Example 9 in Column 14, describing extrusion of a mixture of "Capsul brand dextrin" and beef extract in a Brabender extruder). In using these materials as extrusion encapsulating matrices, the emulsions become too viscous and extrusion pressures in the range of from 800 to 4000+ psi are rquired. The cost limitations imposed by equipment able to generate and withstand extrusion pressures for these materials is prohibitive. Again, as previously indicated, for this and other reasons, the modified starches are not used today commercially as an ingredient in extrusion encapsulation process formulations. According to the present invention, the maximum extrusion pressure is below 150 psi, and usually below 100 psi. The two principal ingredients, when blended together with water and heated, preferably although not essentially under vacuum, to remove 85% or more of the water, form a composition which is normally solid and is soluble in water at ordinary temperatures.

As indicated above, the combination of maltodextrin and "Capsul" enables high loading of active ingredients and extrusion at pressures below 150 psi. None of the prior art of which we are aware suggests or discloses this combination of starch derivatives as a matrix composition for extrusion encapsulating active ingredients.

Another ingredient which is desirably, although not essentially present is an emulsifier. This material is desirably edible, although where insecticides or maturation inhibitors are involved the emulsifying agent may be inedible by humans. In general, the emulsifiers are present in amounts from 0.25 to 5% by weight, and usually from 1% to 3%. Higher levels of emulsifier may be used, but appear not to be beneficial, and at the same time are not harmful. Specific examples of emulsifying agents useful herein include diacetyl tartaric acid ester of a mono-diglyceride of $C_8$–$C_{18}$ fatty acids, e.g., palmitic stearic or oleic acids, ethoxylated mono-diglycerides, mono-diglyceride sodium sulfoacetate, monostearin sodium sulfoacetate, polymeric alkylaryl polyether alcohol, polyethylene glycol oleates or stearates, sodium lauryl sulfate, vegetable oils, glyceryl monooleate, glyceryl monostearate, sorbitan monostearate, acetylated monoglycerides, sodium stearoyl-2-lactylate, citrus stereoptene, lecithin, gum arabic, gum acacia, locust bean gum, guar gum, tragacanth gum, pectin, pectin albedo, agar agar, algin, hydrogenated animal fat, etc. Also useful as emulsifiers are the sulfonate salts, e.g., sodium lauryl sulfonate, sodium petroleum sulfonate, sodium napthalene sulfonate, etc.

BRIEF STATEMENT OF THE INVENTION

Briefly stated, therefore, the present invention is in an encapsulating matrix composition extrudable at a pressure in the range of from about 1 to about 10 atmospheres and having an improved loading capacity up to about 40% comprising (a) from about 5 to about 95 parts by weight of maltodextrin and (b) from about 95 to about 5 parts by weight of hydrogen octenylbutanedioate amylodextrin. Components (a) and (b) total 100 parts by weight. The invention also contemplates a particulate composition comprising the foregoing matrix composition and from about 5% to about 40 weight percent of a normally liquid or volatile active ingredient, such as an organoleptic material. Other ingredients may be present in the basic matrix composition. These include water, emulsifiers, viscosity control agents, e.g., $C_2$–$C_4$ alkylene glycols such as ethylene glycol, propylene glycol, butylene glycol, etc., in effective quantities, generally below 10% by weight.

The role of the modified starch is, primarily, utilization of its lipophilic characteristics to absorb the oil of the active ingredient into the matrix and hold it there. The role of the maltodextrin is to provide matrix bulk and at the same time an emulsion, prior to extrusion, of reasonable viscosity. The relative proportions of these two components can vary within the above ranges, depending upon the loadings and extrusion pressures desired. Preferred proportions are about 80–60 parts and maltodextrin and about 20–40 parts modified starch.

DETAILED DESCRIPTION AND SPECIFIC EXAMPLES

Weight percents as given herein are based on total composition unless otherwise specified.

As indicated above, the principal ingredients of the matrix compositions hereof are individually well known and commercially available as dry powders. Another commercially available modified starch having a low DE is produced by American Maize Products Co. under the name "Amaizo ARD 2326". This material is substantially equivalent to "Capsul" in the environment of this invention. It is described as an octenyl succinic anhydride derivative. Either of these components may be replaced in part with natural gums, e.g., gum acacia, gum arabic, gum tragacanth, etc., corn syrup solids having a DE below about 40, or sucrose. Up to 25% by weight of the component may be so replaced. It should be noted, particularly with reference to edible compositions, that sucrose can be omitted or included as desired, and it is thus possible to produce "sugar-free" or sweetened compositions. Instead of sucrose, equivalent amounts of saccharin, cyclamate, aspartame, fructose, glucose, cellulose compounds, or polyhydric alcohols (e.g., sorbitol, mannitol) or the like, may be used. The principal ingredients may also be mixed in such a way as to provide timed release and various batches of encapsulate blended to provide timed release over a period of time.

Modified starches, such as "Capsul" above described, have several advantages over the current edible sucrose-maltodextrin systems. Total replacement of the sucrose with "Capsul" or its equivalent results in a sugar-free product and enables use in consumer food products making that claim. Inversion of sucrose is a primary factor causing hygroscopicity of the finished product. The presence of sucrose in the encapsulating system limits the length of the cook, the extrusion time and the cook temperature because of each of these parameters affects the degree of inversion. Finished products produced at higher temperatures and/or longer cook and extrusion times tend to be hygroscopic, sticky and unacceptable.

Replacement of part or all of the sucrose with Capsul or the like, reduces or eliminates sucrose inversion and attendant sensitivity to ambient moisture. Also larger batch sizes can be handled and processing times and temperatures made less critical. Flavor systems containing high levels of water (fruit essences) can be encapsulated in accordance with this invention. For example, orange juice concentrate containing 42% water can be encapsulated at 10–15% loading levels. With current sucrose systems, 5 to 6% loading and 20% water is about the limit. No other encapsulation system presently known to us is satisfactory for fruit essences. Highly volatile materials, such as dimethyl sulfide, can be encapsulated in the present systems at a 10% level. Current encapsulating systems enable only one half that amount of dimethyl sulfide.

Many flavor systems include high levels of propylene glycol. Such systems cannot be encapsulated successfully in current sucrose containing systems. Propylene glycol has the same adverse effect on sucrose containing systems as water; it makes the end product sticky and non-functional. However, with the systems of the present invention, loadings of propylene glycol of 15–20% by weight can be obtained.

It should be noted that the addition of propylene glycol for viscosity control, up to 10% by weight, mentioned above, is in addition to the propylene glycol incidentally present in the flavor system. By way of example, the composition of this invention may contain about 20% maltodextrin, about 30% Capsul, and about 40% flavor, of which 20% is oil and 80% is carrier (propylene glycol). Thus, the propylene glycol added to the matrix, via the flavor, is about 32%. It may still be desirable to add a viscosity controlling amount, for instance about 5% of additional propylene glycol for viscosity control, the balance being emulsifiers or the like.

Again, the present invention contemplates active ingredient loadings of from about 5 to about 40% by weight. For purposes of this application, the term "active ingredient" means active agent plus carrier, for instance flavor plus water, or propylene glycol.

Because of the nonhygroscopic nature of the present systems, the need for anticaking agents is reduced.

Regarding the active ingredients of the emulsion, one may employ many different volatile flavoring agents, for example orange oil, lemon oil, grapefruit oil, lime oil, clove oil, peppermint oil, bay oil, cedarwood oil, ethanol fruit essence extracts such as apple essence, pear essence, pineapple essence, grape essence, peach essence, apricot essence, strawberry essence, raspberry essence, cherry essence, prune essence, plum essence, cinnamon oil, oil of nutmeg, oil of sage, oil of bitter almonds, cassia oil, teaseed oil, coffee essence, and so forth. Mixtures of different flavoring agents may of course be employed. In the case of fruit essences, such as those enumerated above, it is preferable to first purify them to remove water and low-molecular weight alcohols. It is also preferred to add an edible oil and/or an edible emulsifying agent to the purified fruit essence so that it will emulsify properly with the matrix. Instead of or together with natural flavoring principles, synthetic flavoring agents may be employed. Examples are the edible flavor and aroma bearing aldehydes, alcohols, esters, ketones, phenols, and lactones, for instance methyl anthranilate, decanal, nonanal, undecanal, cinnamic aldehyde, geraniol, menthol, methyl salicylate, phenylethyl alcohol, diacetyl, citronellol, citral, and so forth.

The proportion of flavoring agent to be incorporated in the carrier base may be varied depending on the flavor strength desired in the final product. As indicated above, the active agents in the encapsulants of the present invention may be organoleptics, e.g., flavors or fragrances, agricultural chemicals, e.g., insecticides, fertilizers, flavor enhancers, e.g., acetaldehyde or citral, growth hormones, maturation inhibitors, etc., and pharmaceuticals, with or without carriers. These encapsulating matrices materials are soluble in water to release the active ingredient. They may be used as ingredients of candy or lozenges, or breath deodorants. The active ingredients useful herein are desirably normally liquid and form a distinct dispersed phase in the hot matrix.

The method of preparing the encapsulates of the present invention is analogous to that in U.S. Pat. No. 3,704,137 to Beck.

In essence, a tank is provided, having heating and agitating means, to effect the steps of mixing, cooking and cooling. Initially, the matrix ingredients, water and other ingredients such as emulsifying agent and viscosity controlling agent, if desired, are charged into the tank, and the mass is stirred and subjected to heating or cooking, under a vacuum effective to remove water, until the boiling point of the mixture reaches, by way of example, about 104°–116° C. At this point, the cook is terminated and the active ingredient is added, in the amount of about 5–40 weight percent. Mixing is carried out until complete, still at about the same elevated temperature, since no substantial cooling takes place.

In the above procedure, the amount of water used initially is a solubilizing amount, sufficient to solubilize the matrix ingredients. During the boiling, the amount is reduced to about 3–12%, for instance about 10%, depending in part upon proportions of ingredients and viscosity desired (for the susequent extrusion step). The vacuum selected for the boiling or cooking step is dependent in part on the active ingredient to be added. Cooking at 120° C. would prevent adding a highly volatile active ingredient to the cook solution. A typical vacuum may be about 685 mm Hg.

Use of a higher vacuum permits boiling at a temperature even as low as about 70°–80° C., permitting use of even more volatile active ingredients.

Once the active ingredient is added the composition it is in the form of an emulsion or slurry, depending upon whether the active ingredient is oil based or water based.

The cooking tank is provided with an extrusion cap or spinneret, isolated from the tank by a valve. Opening the valve allows the tank contents to move under pressure through the extrusion cap or spinneret into a basket carried in a shallow tray of cold solvent for the active ingredient, such as isopropyl alcohol. The extruder has a head provided with a large number of about 1/64 inch diameter orifices through which the combined mix is forced under 20 to 150 psig air pressure. The cold solvent serves two purposes, to remove excess active ingredient from the surface of the extrudate, and to effect solidification of the extruded melt (an example of a solvent temperature effective to solidify the extrudate is about −10° C.). In the tank, the extruded rods can be subjected to agitation and comminution to wash off the excess oil, and also to break up the rods into desired lengths. From the tank, the broken-up rods are separated from a major portion of the liquid solvent by a settling or draining action, and the broken-up rods are then charged into a centrifuge to remove most of the liquid solvent, the solvent being discharged from the centrifuge into a solvent tank.

The particulate, rod-like solids from the centrifuge are discharged into a mixer, into which is also charged an anticaking agent. The preferred anticaking agent is siliceous material, preferably pyrogenic silica, of a particle size comparable to that desired in the final essential oil composition of my invention. The anti-caking agent is incorporated into the melt mix prior to drying and screening, but the siliceous material can be added to the liquid solvent prior to extrusion or can be added to the rod-like particles after the centrifuging step.

The finished product contains an amount of essential oil up to about 40% of oil by weight of the finished product. The product has good keeping properties in that it will not crystallize upon long standing, nor is it subject to substantial deterioration if suitably packaged and protected by antioxidants. The use of about 0.5% by weight of the final composition of pyrogenic silica powder effectively prevents the rod-like particles of the composition from sticking together upon long standing in a packaged condition and, also, of course, facilitates the transfer of the composition from the packages to the points of actual use of the composition.

The following examples are illustrative of the mode of making the compositions of this invention. All temperatures are in degrees Celsius and all percents are by weight unless otherwise stated.

EXAMPLE I

The following ingredients in the amounts indicated were stirred together at room temperature to form a uniform liquid blend: This example represents the best mode of practicing our invention presently known to us.

| | |
|---|---|
| Maltodextrin | 1940 grams |
| "Capsul" | 485 grams |
| Polyglycerol esters of C$_6$-C$_{10}$ fatty acid (emulsifying agent) | 150 grams |
| Water | 1880 grams |

This mixture was placed in a steel vessel fitted with a thermometer, a stirrer, an inlet tube and an exhaust and provided with heating and vacuum means. The mass was charged into the vessel, stirred, a vacuum of 685 mm created and the cook continued until the temperature reached 110° C. Water is continually removed. The cook was terminated and at atmospheric pressure, 982 grams of orange oil was added. Mixing was carried on for 10 to 20 minutes at 110° C. An extrusion cap or spinneret is fitted on the apparatus and isolated from the balance of the apparatus by a valve. Opening the valve allows the contents to move through the spinneret and into a basket carried in a shallow tray of cold isopropyl alcohol. Extrusion was done under nitrogen pressure of 20 to 100 psi over a period of 10 to 20 minutes and at a temperature of 105° C. to 110° C. The rod-like extrudate was captured in a basket immersed in cold (−20° to 23° C.) alcohol and the resulting extruded rods broken with a suitable beater to provide particulate encapsulated orange oil. Excess oil is removed from the exterior of the particles and can be recovered for recycling. The particles may be washed with more alcohol and centrifuged. The resultant granular powder is dried at a temperature not over about 38° C. for a period of 2 hours at a temperature sufficient to volatilize the isopropyl alcohol. An anticaking agent, such as pyrogenic silica, calcium sulfate, montmorillonite clay, or the like, may be added in an amount of about 1%–2%, if desired. The product is then screened to desired size and packaged. Further details of the process and apparatus will be found in U.S. Pat. No. 3,704,137, supra. Alternative emulsifying agents that may be used instead of the polyglyceryl esters of fatty acids are exemplified in Swisher U.S. Pat. No. 3,041,180. The loading level was 24.2% by weight. In use, the flavor can be released by disolving the particulate product in water or an aqueous medium.

This example illustrates the high loading capability of the matrices of the present invention.

EXAMPLE II

The procedure of Example I is interrupted at the point just prior to introduction of the essential oil, and the encapsulation matrix material extruded per se. This material is useful as a powder diluent for encapsulated active agents in dry application in the case of agricultural chemicals. In this case no emulsifier is necessary. The ultimate water content is from 5 to 8% by weight.

EXAMPLE III

The following ingredients in the amounts indicated were treated in the manner set forth in Example I, except where indicated.

| Maltodextrin | 468 grams |
| "Capsul" | 117 grams |
| Emulsifier* | 10 grams |
| Water | 450 grams |
| Orange Juice 58° Conc. | 115 grams |

*See Example I.

Extrusion was carried out at 105° C. to 110° C. under 40 psi nitrogen.

This example illustrates the application of the invention to high moisture fruit flavors. The loading level was 15%. The juice is released on dissolution in water.

EXAMPLE IV

This example is like Example III except that 72 grams of propylene glycol are substituted for the orange juice. Extrusion was carried out at 105° C. to 110° C. at 20 psi of nitrogen. The resultant granular product carried a loading of propylene glycol of 10%. The viscosity control agent, propylene glycol, is useful in the extrusion step. When the material is dissolved in water in its ultimate use, the propylene glycol is released but is regarded as safe for human consumption.

EXAMPLE V

Following the procedure set forth in Example I, the following ingredients in the amounts indiindicated were blended, cooked and extruded.

| Maltodextrin | 1940 grams |
| "Capsul" | 485 grams |
| Emulsifier* | 80 grams |
| Water | 1880 grams |

The cook was carried out to 109° C. and 300 grams of dimethyl sulfide injected under pressure from a nitrogen pressurized vessel. After mixing, extrusion was carried out at 100° C. to 110° C. at 50 psi nitrogen.

This example illustrates the encapsulation of a low boiling point (37° C.) material. The loading was found to be 3.45% by weight.

EXAMPLE VI

Following the procedure of Example I, the following ingredients in the amounts indicated were blended, cooked and extruded.

| Maltodextrin M-100 | 2304 grams |
| Amaizo ARD 2326 | 121 grams |
| Emulsifier* | 80 grams |
| Water | 1880 grams |
| Orange oil | 440 grams |

*Emulsifier of Example I

Cooking was carried out to 105° C.–110° C.; extrusion was at 105°–110° C. at 20 psi nitrogen. The loading in this case was found to be 15.12% by weight.

EXAMPLE VII

Following the procedure of Example I, the following ingredients in the amounts indicated were blended, cooked and extruded.

| Maltodextrin M-100 | 526 grams |
| Amaizo ARD 2326 | 58 grams |
| Emulsifier* | 34 grams |
| Water | 450 grams |
| Lemon oil | 175 grams |

Cooking was carried out to 105°–110° C.; extrusion was at 105°–110° C. at 20 psi nitrogen. The loading in this case was 12.4% by weight.

EXAMPLE VIII

Following the procedure of Example I, the following ingredients in the amounts indicated were blended, cooked and extruded.

| Maltodextrin M-100 | 407 grams |
| Staley Modified Starch | 175 grams |
| Emulsifier* | 35 grams |
| Water | 450 grams |
| Orange oil | 125 grams |

*Emulsifier of Example I

The cook temperature reached 105°–110° C.; extrusion was carried out at 105°–110° C. at 20 psi nitrogen. The extrudate when washed and dried had an oil loading of 16% by weight. The product is used by addition to water or an aqueous medium.

EXAMPLE IX

Following the procedure of Example I, the following ingredients in the amounts indicated are blended, cooked and extruded:

| | |
|---|---|
| Maltodextrin | 1940 grams |
| "Capsul" | 400 grams |
| Sucrose | 100 grams |
| Glyceryl monosterate | 100 grams |
| Water | 1900 grams |
| Lemon oil | 125 grams |

The cook temperature is carried to 105°-110° C. and extrusion carried out at the same temperature at 50 psi nitrogen. This yields a sugar sweetened encapsulate of lemon oil.

We claim:

1. A particulate composition in the form of a solid extrudate comprising a matrix composition and up to about 40% loading, based on the weight of the particulate composition, of an active ingredient, wherein said matrix composition comprises
    (a) from about 5 parts to about 95 parts by weight of maltodextrin; and
    (b) about 95 parts to about 5 parts by weight of hydrogen octenyl butanedioate amylodextrin, the combined weight of (a) and (b) being 100 parts.

2. The particulate composition of claim 1 prepared by extrusion from a hot cook solution, wherein said cook solution contains about 3-12% water and is extrudable at a pressure in the range of about 1-10 atmospheres.

3. The particulate composition of claim 2, wherein said hot cook solution is extruded into a cold solvent for the active ingredient.

4. The particulate composition of claims 1 or 3 wherein said composition is free of active ingredient on the surface thereof.

5. The particulate composition of claim 1 wherein the active ingredient is a fruit essence.

6. The particulate composition of claim 1 wherein said active ingredient is an essential oil composition.

7. An encapsulating matrix composition extrudable at a pressure ranging from 1 to 10 atmospheres and having improved loading capacity comprising (a) from about 5 to about 95 parts by weight of maltodextrin and (b) from about 95 to about 5 parts by weight of hydrogen octenyl butanedioate amylodextrin, the combined weight of (a) and (b) being 100 parts by weight.

8. An encapsulating matrix composition as defined in claim 7 wherein component (a) is present in the range of from about 80 to about 60 parts by weight and component (b) is present in the range of about 20 to about 40 parts by weight.

9. An encapsulating matrix composition as defined in claim 7 wherein a part of component (b) is replaced with a mono- or disaccharide.

10. An encapsulating matrix composition as defined in claim 9 wherein the disaccharide is sucrose.

11. An encapsulating matrix composition as defined in claim 7 wherein the matrix composition also contains from about 0.25 to about 5 parts by weight of an emulsifier.

12. An encapsulating matrix composition as defined in claim 11 wherein the emulsifier is a mono-glyceride of stearic or oleic acid, a diglyceride or stearic or oleic acid, or a mixed mono-diglyceride of stearic or oleic acid.

13. An encapsulating matrix composition as defined in claim 11 wherein the emulsifier is a polyglycerol ester of a $C_6$ to $C_{18}$ fatty acid.

14. An encapsulating matrix composition as defined in claim 1 in slurry form wherein said composition further includes a viscosity controlling amount of an alkylene glycol.

15. An encapsulating matrix composition as defined in claim 14 wherein said alkylene glycol is a $C_2$ to $C_4$ glycol.

16. An encapsulating matrix composition as defined in claim 15 wherein the glycol is propylene glycol.

17. A method of preparing a stable, particulate essential oil composition, comprising the steps of
    (1) agitating and boiling a mixture of
        (a) from about 5 to about 95 parts by weight of maltodextrin;
        (b) from about 95 to about 5 parts by weight of hydrogen octenyl butanedioate amylodextrin; and
        (c) water; to form an encapsulating matrix composition, the combined weights of (a) and (b) being 100 parts by weight;
    (2) mixing an active ingredient with said matrix composition to form a slurry or emulsion composition;
    (3) extruding said slurry or emulsion composition into a cold solvent for the active ingredient to form an extrudate, the solvent being at a temperature effective to solidify the extrudate; and
    (4) comminuting the extrudate;
    the extrusion being carried out at a pressure in the range of about 1-10 atmospheres.

18. The method of claim 17 wherein said slurry composition comprises up to about 40 percent by weight active ingredient.

19. The method of claim 18 wherein said active ingredient is an essential oil composition.

20. The method of claim 19 wherein said essential oil composition comprises essential oil plus carrier.

21. The method of claim 20 wherein said carrier is propylene glycol.

22. The method of claim 17 wherein said matrix composition comprises about 80 to about 60 parts by weight of (a) and about 20 to about 40 parts by weight of (b).

23. The method of claim 17 or 22 wherein said matrix composition further comprises a viscosity controlling amount of an alkylene glycol.

24. The method of claim 17 or 22 wherein said matrix composition further comprises an emulsifying amount of an emulsifier.

25. The method of claim 17 or 22 wherein said matrix composition further comprises a carbohydrate in a flavoring or bulking amount.

26. The method of claim 17 or 22 wherein said matrix composition further comprises a natural gum in a bulking amount.

27. The method of claim 25 wherein said carbohydrate is a mono- or disaccharide.

28. The method of claim 24 wherein said emulsifier is (a) a monoglyceride of stearic or oleic acid; or (b) a mono-diglyceride of stearic or oleic acid; or (c) a polyglycerol ester of a $C_6$ to $C_{18}$ fatty acid.

* * * * *